United States Patent
Jang et al.

(10) Patent No.: US 10,750,964 B2
(45) Date of Patent: Aug. 25, 2020

(54) METHOD FOR ANALYZING BLOOD FLOW BY USING MEDICAL IMAGE

(71) Applicant: THE CATHOLIC UNIVERSITY OF KOREA INDUSTRY-ACADEMIC COOPERATION FOUNDATION, Seoul (KR)

(72) Inventors: Jin Hee Jang, Seoul (KR); Yoon Ho Nam, Seoul (KR); Bum Soo Kim, Seoul (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 71 days.

(21) Appl. No.: 16/074,636

(22) PCT Filed: Jan. 25, 2017

(86) PCT No.: PCT/KR2017/000883
§ 371 (c)(1),
(2) Date: Aug. 1, 2018

(87) PCT Pub. No.: WO2017/135635
PCT Pub. Date: Aug. 10, 2017

(65) Prior Publication Data
US 2019/0038150 A1 Feb. 7, 2019

(30) Foreign Application Priority Data
Feb. 4, 2016 (KR) .................. 10-2016-0014162

(51) Int. Cl.
*A61B 5/026* (2006.01)
*A61B 5/02* (2006.01)
(Continued)

(52) U.S. Cl.
CPC .............. *A61B 5/0263* (2013.01); *A61B 5/00* (2013.01); *A61B 5/02* (2013.01); *A61B 5/026* (2013.01);
(Continued)

(58) Field of Classification Search
CPC ........... A61B 5/0263; A61B 5/00; A61B 5/02; A61B 5/026; A61B 5/055; A61B 5/7278;
(Continued)

(56) References Cited

U.S. PATENT DOCUMENTS 8,837,800 B1 * 9/2014 Bammer ................. G06T 7/337
382/130
2010/0056936 A1 3/2010 Fujii et al.
(Continued)

FOREIGN PATENT DOCUMENTS

JP 07-092184 A 4/1995
JP 2003-019119 A 1/2003
(Continued)

OTHER PUBLICATIONS

Ferreira, R.M., Lev, M.H., Goldmakher, G.V., Kamalian, S., Schaefer, P.W., Furie, K.L., Gonzalez, R.G. and Sanelli, P.C., 2010. Arterial input function placement for accurate CT perfusion map construction in acute stroke. American Journal of Roentgenology, 194(5), pp. 1330-1336.*

*Primary Examiner* — Zhitong Chen
(74) *Attorney, Agent, or Firm* — Novick, Kim & Lee, PLLC; Sang Ho Lee

(57) ABSTRACT

Provided is a technique for deriving a mathematical function for defining arterial and venous blood flow in the body by using a four-dimensional medical image. A method of analyzing blood flow by using a medical image according to an embodiment of the present disclosure includes: determining a position of a blood vessel from four-dimensional medical
(Continued)

image data that is obtained by combining data of three-dimensional medical images of a patient's body captured at a preset period; deriving a primary function for an arterial input function and a venous output function by using a vascular signal in a head region and a vascular signal in a heart region from among vascular signals included in three-dimensional medical image data for the position of the blood vessel determined in the determining; and deriving a secondary function that is a final function for the arterial input function and the venous output function by using the primary function and a vascular signal in a neck region.

4 Claims, 8 Drawing Sheets

(51) Int. Cl.
| | |
|---|---|
| *A61B 5/055* | (2006.01) |
| *A61B 5/00* | (2006.01) |
| *G06T 7/11* | (2017.01) |
| *G01R 33/56* | (2006.01) |
| *G01R 33/563* | (2006.01) |
| *G06T 7/00* | (2017.01) |
| *A61B 6/00* | (2006.01) |
| *G01R 33/48* | (2006.01) |

(52) U.S. Cl.
CPC .......... *A61B 5/055* (2013.01); *G01R 33/5601* (2013.01); *G01R 33/5635* (2013.01); *G06T 7/0012* (2013.01); *G06T 7/11* (2017.01); *A61B 5/7278* (2013.01); *A61B 6/504* (2013.01); *G01R 33/4818* (2013.01); *G01R 33/56366* (2013.01); *G06T 2207/20032* (2013.01); *G06T 2207/30104* (2013.01)

(58) Field of Classification Search
CPC ......... A61B 6/504; G06T 7/11; G06T 7/0012; G06T 2207/20032; G06T 2207/30104; G01R 33/5601; G01R 33/5635; G01R 33/4818; G01R 33/56366
See application file for complete search history.

(56) References Cited

U.S. PATENT DOCUMENTS

2016/0166159 A1* 6/2016 Yang ...................... G06T 7/11
600/419
2016/0245889 A1* 8/2016 Djeridane ........ G01R 33/56366

FOREIGN PATENT DOCUMENTS

| KR | 10-2010-0133996 A | 12/2010 |
| KR | 10-2015-0113157 A | 10/2015 |

* cited by examiner

METHOD FOR ANALYZING BLOOD FLOW BY USING MEDICAL IMAGE

TECHNICAL FIELD

The present disclosure relates to a technology for analyzing a blood flow within a blood vessel in a body by using a medical image such as a magnetic resonance (MR) or computed tomography (CT) image, and more particularly, to a technology for deriving a function for defining a blood flow in a vein and an artery in a body by using an image that is captured of the inside of the body by injecting a contrast medium into the body.

BACKGROUND ART

A phase contrast magnetic resonance imaging (MRI) technique using an MRI apparatus have been widely used for noninvasive measurement of fluid flow within the human body, such as blood flow. This technique is used to acquire a reference image that does not reflect a velocity by using a gradient pulse that sets an image of a blood flow velocity to zero immediately after an R-wave of an electrocardiogram (ECG) and to acquire a velocity encoded image that have reflected a blood flow velocity by using a velocity encoding gradient. Then, a reference image and a velocity encoded image are captured. Pairs of the reference image and the velocity encoded image are continuously captured during one cycle of the ECG and until k-space is fully filled by varying the magnitude of phase encoding gradients. Then, velocity images are reconstructed from the captured images and are used to measure a blood flow velocity during one cycle of the ECG.

However, this technique has problems that only a blood flow velocity can be measured in analyzing blood flow and it is insufficient to represent a high temporal resolution and accurate blood flow.

To solve the problems, a technique for analyzing arterial and venous flow has been proposed in U.S. Pat. No. 8,837,800, etc. The proposed technique includes: selecting some of the pixels of an image in order to derive an arterial input function (AIF) and a venous output function (VOF) based on a medical image; normalizing signals in the pixels; and derive the AIF and the VOF in a blood vessel composed of pixels by using a Gaussian transform.

However, this conventional technique has problems that an AIF and a VOF cannot be accurately derived, and errors may occur. Another problem is that the technique cannot accurately identify a blood vessel from a medical image, thereby hampering analysis of blood flow in the blood vessel.

DESCRIPTION OF EMBODIMENTS

Technical Problem

Provided is a technology for accurately analyzing blow flow in arteries and veins by deriving an arterial input function and a venous output function with high accuracy. The arterial input function and venous output function may be accurately derived by accurately recognizing a blood vessel from a medical image generated during imaging of the inside of the body via magnetic resonance imaging (MRI), time-resolved magnetic resonance angiography (TRMRA), CT, etc., by injecting a contrast medium, and analyzing the blood vessel by using a novel technique.

Solution to Problem

According to an aspect of the present disclosure, there is provided a method of analyzing blood flow by using a medical image, the method including: determining a position of a blood vessel from four-dimensional medical image data that is obtained by combining data of three-dimensional medical images of a patient's body captured at a preset period; deriving a primary function for an arterial input function and a venous output function by using a vascular signal in a head region and a vascular signal in a heart region from among vascular signals included in three-dimensional medical image data for the position of the blood vessel determined in the determining; and deriving a secondary function that is a final function for the arterial input function and the venous output function by using the primary function and a vascular signal in a neck region.

Advantageous Effects of Disclosure

According to the present disclosure, it is possible to accurately detect a position of a blood vessel by using a change in signal magnitude for each time frame in four-dimensional medical image data including three-dimensional images captured at different time frames and accurately analyze an arterial input function and a venous output function based on a signal magnitude in the blood vessel. In particular, it is possible to derive highly accurate arterial input function and venous output function by using vascular signals in a neck region.

In other words, by analyzing a medical image with a novel technique to allow accurate analysis of blood flow, it is possible to extract various pieces of information related to hemodynamics by using a mathematical model. The mathematical model may also be effectively used in a visualization process such as generating an image and a difference image at a meaningful specific time point.

BEST MODE

Figure 1:
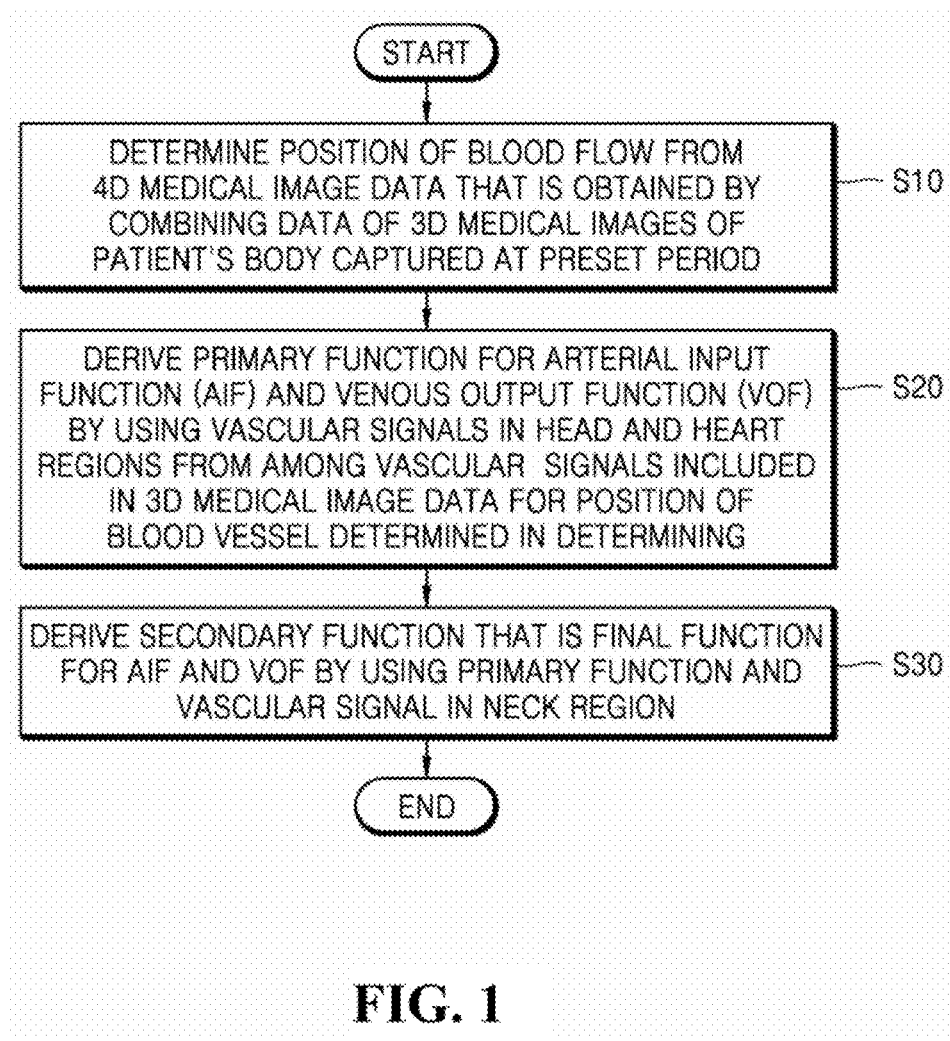
FIGS. 1 through 4 are flowcharts of a method of analyzing blood flow by using a medical image, according to an embodiment of the present disclosure.

Hereinafter, a method of analyzing blood flow by using a medical image according to embodiments of the present disclosure will be described more fully with reference to the accompanying drawings.

It should be understood that embodiments described hereinafter are provided for better understanding of the present disclosure and not for purposes of limitation. Thus, equivalent inventions which perform substantially the same functions as the present disclosure will be included in the scope of the present disclosure.

In adding reference numerals to components on each drawing, it should be noted that the same elements will be designated by the same reference numerals although they are shown in different drawings. Furthermore, in the following description of the present disclosure, a detailed description of known functions and configurations incorporated herein will be omitted when it may make the subject matter of the present disclosure rather unclear.

In addition, terms, such as first, second, A, B, (a), (b) or the like may be used herein when describing components of the present disclosure. Each of these terminologies is not used to define an essence, order or sequence of a corresponding component but used merely to distinguish the corresponding component from other component(s). It should be understood that when one component is "connected," "joined," or "coupled" to another component, the one component may be directly connected, joined, or coupled to the other component, or a third component may be "connected," "joined," or "coupled" between the two components.

FIGS. 1 through 4 are flowcharts of methods of analyzing blood flow by using a medical image, according to embodiments of the present disclosure.

Referring to FIG. 1, a method of analyzing blood flow by using a medical image according to an embodiment of the present disclosure may be performed by a terminal capable of processing data, such as a computer or other devices that receive image data from a medical image capturing device.

In the method of analyzing blood flow by using a medical image according to the embodiment, first, a position of a blood vessel is determined from four-dimensional (4D) medical image data that is obtained by combining data of three-dimensional (3D) images of a patient's body captured at a preset period (S10). The patient's body imaged in step S10 preferably includes the head to the chest region near the heart, but is not limited thereto.

In the present disclosure, for example, the 4D medical image data may be data acquired using time-resolved magnetic resonance angiography (TRMRA). TRMRA is a type of MRA using an MR image and may be used to observe a change in a vascular signal over time. In an experiment related to an embodiment of the present disclosure, this technique may be used to obtain an image every two (2) seconds or so. In addition to the TRMRA technique, all other techniques capable of acquiring 4D medical image data by obtaining 3D images at specific time intervals may be used.

A method of acquiring a vascular signal in an image by determining a position of a blood vessel based on medical image data may be performed using a signal change during injection of a contrast medium in MRA.

In detail, in the step S10 of determining the position of the blood vessel, among pixels constituting the 4D medical image data, pixels ranked in a high place of a preset ratio in an order of a difference value between the maximum value and the minimum value of a signal magnitude according to time, are determined as pixels constituting the blood vessel.

When a contrast medium is injected during MRA, signal intensity rapidly increases at a position that the contrast medium reaches during use of an appropriate imaging technique. Accordingly, when a TRMRA image having a temporal resolution is obtained after administration of the contrast medium, hemodynamic information may be acquired based on signal variations due to administration of the contrast medium.

Thus, pixels in a high place having a large signal difference, e.g., 10% are determined as pixels acquired by imaging the blood vessel. An example thereof will now be described in more detail with reference to FIG. 5.

Figure 5:
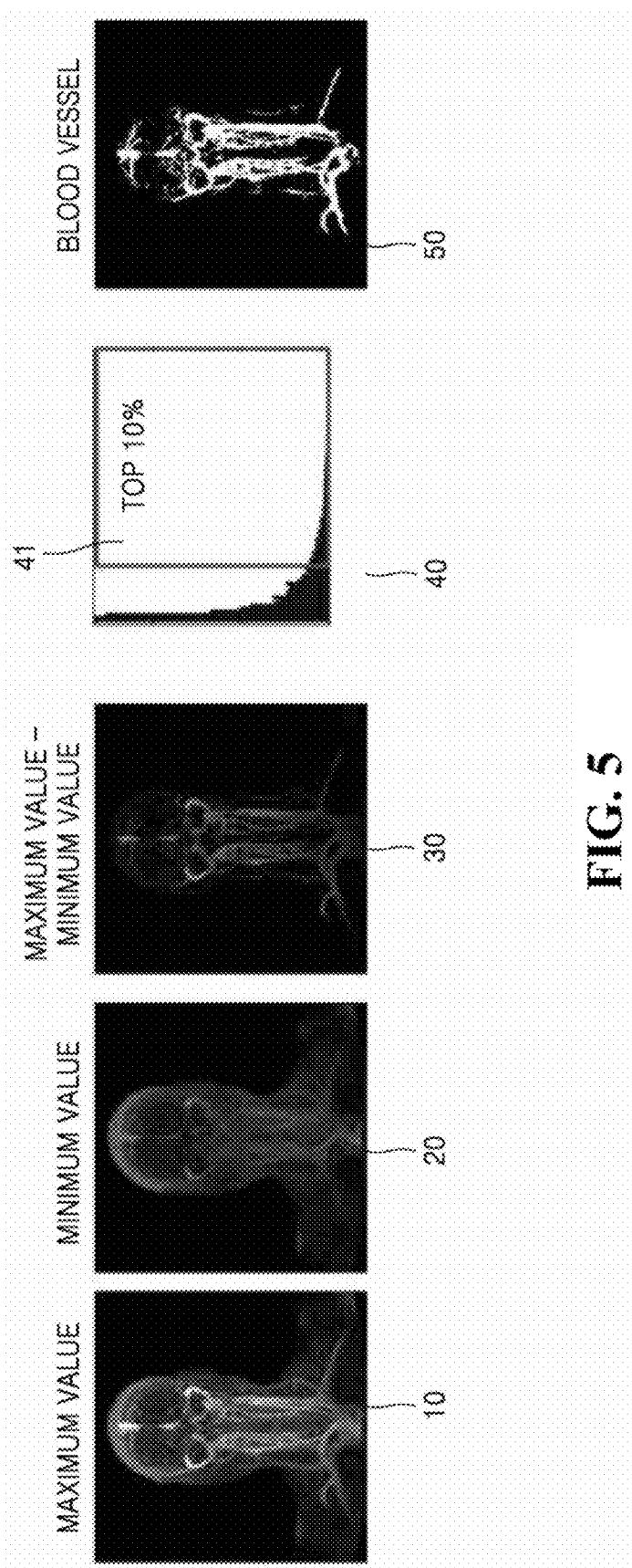
FIGS. 5 through 8 illustrate that blood flow is analyzed according to an implementation of the embodiment.

Referring to FIG. 5, image data having maximum data 10 and minimum data 20 of signals are extracted from 3D image data captured after administration of a contrast medium. Subsequently, image data 30 having a difference between a maximum value and a minimum value of the signal is generated or extracted. After analyzing such differences as a graph 40, pixels having differences 41 corresponding to a predetermined ratio, e.g., top 10% in a descending order of differences are selected. A part of image data corresponding to the selected pixels is determined as blood vessel data 50.

Returning to the description with reference to FIG. 1, after performing step S10, a primary function for an arterial input function (AIF) and a venous output function (VOF) is derived by using a vascular signal in a head region and a vascular signal in a heart region from among vascular signals included in 3D medical image data for the position of the blood vessel determined in step S10 (S20).

As described above, medical image data used herein is data acquired by imaging a body part from a patient's head through a chest region. The AIF and VOF are functions defined for analysis of images chronologically obtained after administration of the contrast medium and are mainly defined as patterns in which signals change over time in main blood vessels.

In this case, during analysis of a brain region, an AIF and a VOF may often be defined in a neck region. However, since blood vessels in the neck region include a mixture of veins and arteries, it is difficult to accurately define an AIF and a VOF. Thus, in the present disclosure, an AIF and a VOF are first defined and then a primary function is corrected by analyzing a vascular signal in a neck region to finally derive the AIF and the VOF.

In deriving the primary function, the following conditions are applied: i.e., an average of vascular signals near the heart in 4D medical image data will mostly reflect an AIF while an average of vascular signals at the head will mostly reflect a VOF.

Figure 3:
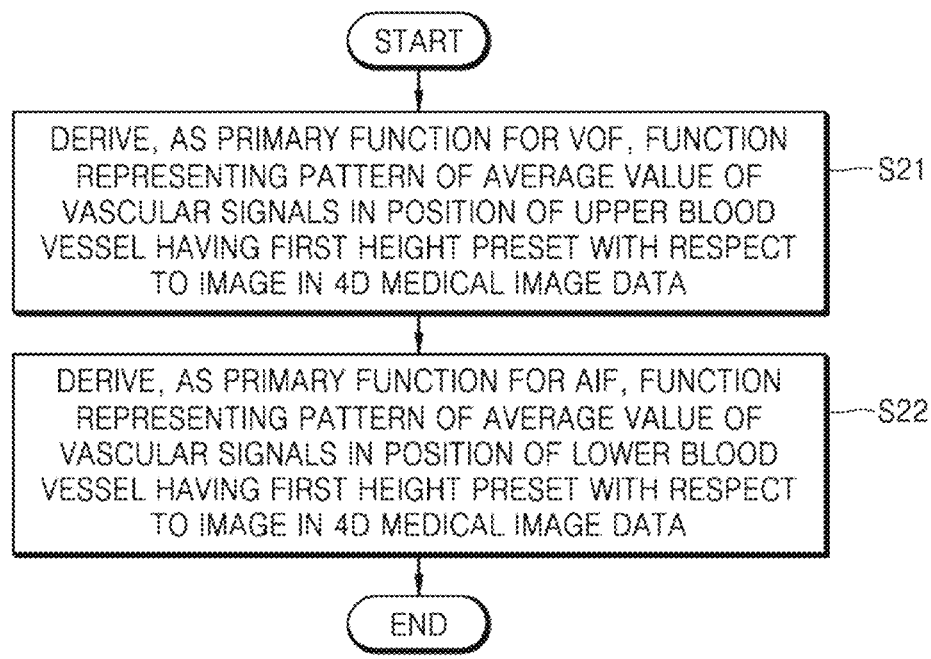
Figure 7:
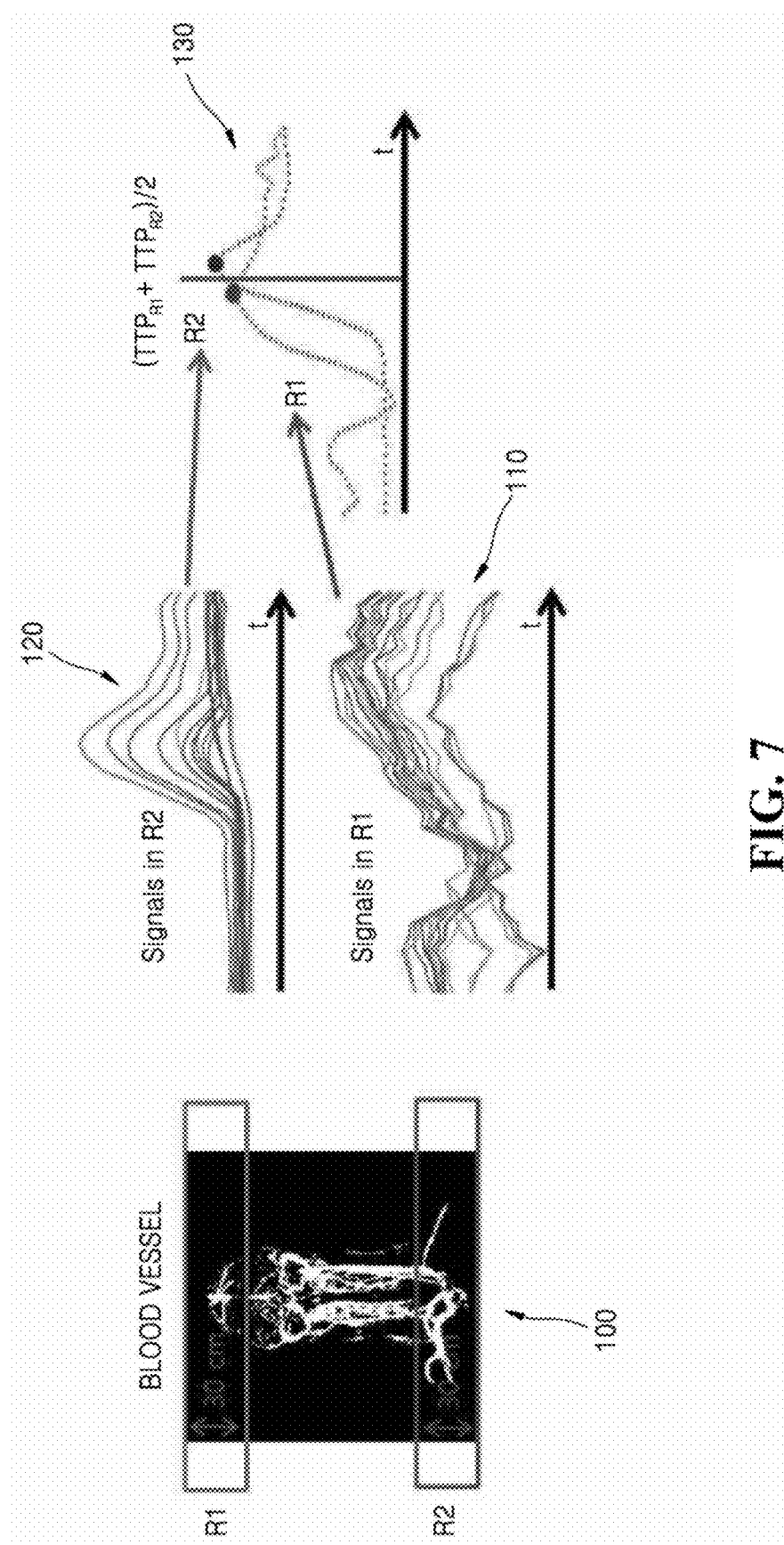

By using the conditions, the primary function is derived as in an example shown in FIGS. 3 and 7.

Referring to FIGS. 3 and 7, first, a function, which represents a pattern of an average value of vascular signals 110 in a position R1 of an upper blood vessel at a first height preset with respect to an image in 4D medical image data 100, is derived as a primary function for a VOF (S21).

In addition, a function, which represents a pattern of an average value of vascular signals 120 in a position R2 of a lower blood vessel at the first height preset with respect to the image in the 4D medical image data 100, is derived as a primary function for an AIF (S22), together with the primary function for the VOF.

A primary function 130 is obtained using the above-described assumption, and the primary function 130 may include an AIF (R2 of 130) and a VOF (R1 of 130). The above-described process is performed to identify arteries and veins, thereby accurately distinguishing blood vessels from one another.

Returning to the description with reference to FIG. 1, after deriving the primary function in step S20, a secondary function that is a final function for the AIF and the VOF is obtained using the derived primary function and a vascular signal in a neck region among the vascular signals (S30).

Vascular signals in regions other than the neck region may be analyzed depending on a body part in which blood flow is to be analyzed using an AOF and a VOF. However, for analysis of a brain region, an AIF and a VOF are defined mostly in the neck region.

Accordingly, the primary function for the head region and the chest region near the heart is corrected according to a vascular signal in the neck region to thereby derive the secondary function as a final function. As described above, it is obvious that the secondary function may be derived based on a vascular signal in other regions according to a body part to be analyzed.

For performing step S30, it is important to define data regarding the neck region among pieces of the 4D medical image data. An embodiment related thereto is shown in FIGS. 2 and 6.

Figure 2:
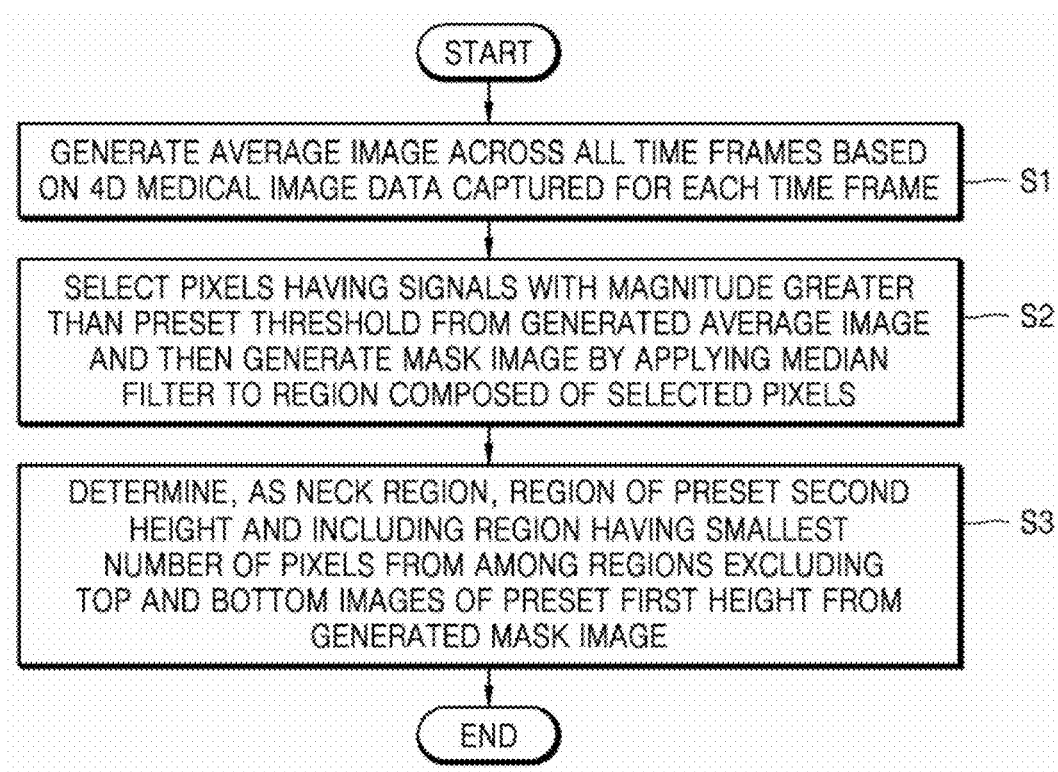
Figure 6:
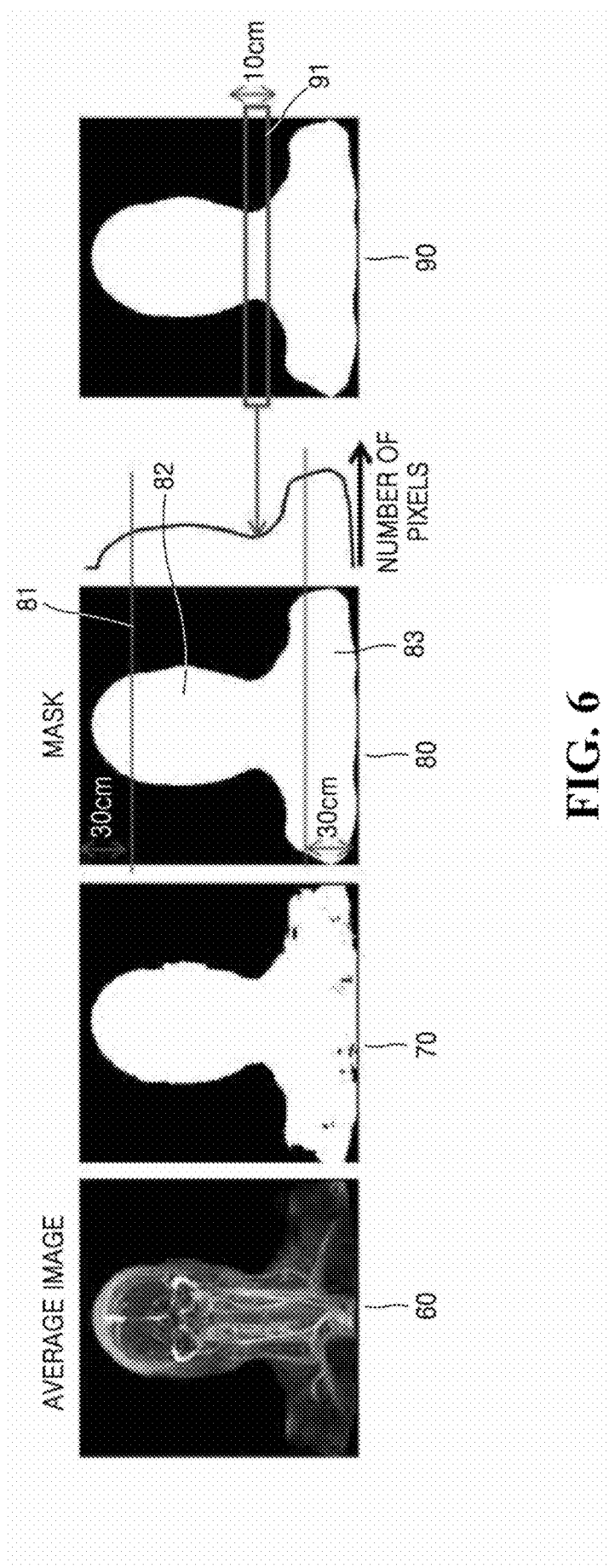

Referring to FIGS. 2 and 6, to determine a neck region, first, an average image 60 across all time frames is generated based on 4D medical image data captured for each time frame (S1).

Subsequently, pixels having signals with a magnitude greater than a preset threshold are selected from the generated average image, and a median filter is then applied to completely fill a region 70 composed of the selected pixels to thereby generate a mask image 80 (S2).

In detail, an initial mask is generated by leaving behind only pixels that are, for example, 0.5 times greater than an average value of signals in the entire area by means of a thresholding technique and removing a background from the average image 60 generated in step S1. Thereafter, a final mask is generated by filling holes remaining in a mask region through median filtering.

After generating a mask in step S2, the number of pixels in the mask is calculated in a direction from a torso toward a head. Next, a region 91 of a preset second height and including a region having the smallest number of pixels from among regions 82 excluding both top and bottom images 81 and 83 of a preset first height from the mask images 80 and 90 is set to be a neck region (S3).

Finding a cross-section including a neck as a criterion of performing step S3 is based on an assumption that a person's neck has a relatively small volume compared to the head and torso. In other words, in determining a neck region based on the number of pixels in an image, to exclude top and bottom portions of the image where errors may occur due to the absence of pixels from candidates for the neck region, the top and bottom images 81 and 83 of the preset first height (e.g., 30 cm) are both excluded from the mask images 80 and 90. Furthermore, the region 91 of the second height (e.g., 10 cm) and including a region with the smallest number of pixels among the remaining regions 82 is set to be the neck region.

Returning to the description with reference to FIG. 1, the secondary function that is a final function for the AIF and VOF is obtained by reflecting the vascular signal in the neck region in the primary function. A detailed embodiment thereof is shown in FIGS. 4 and 8.

Figure 4:
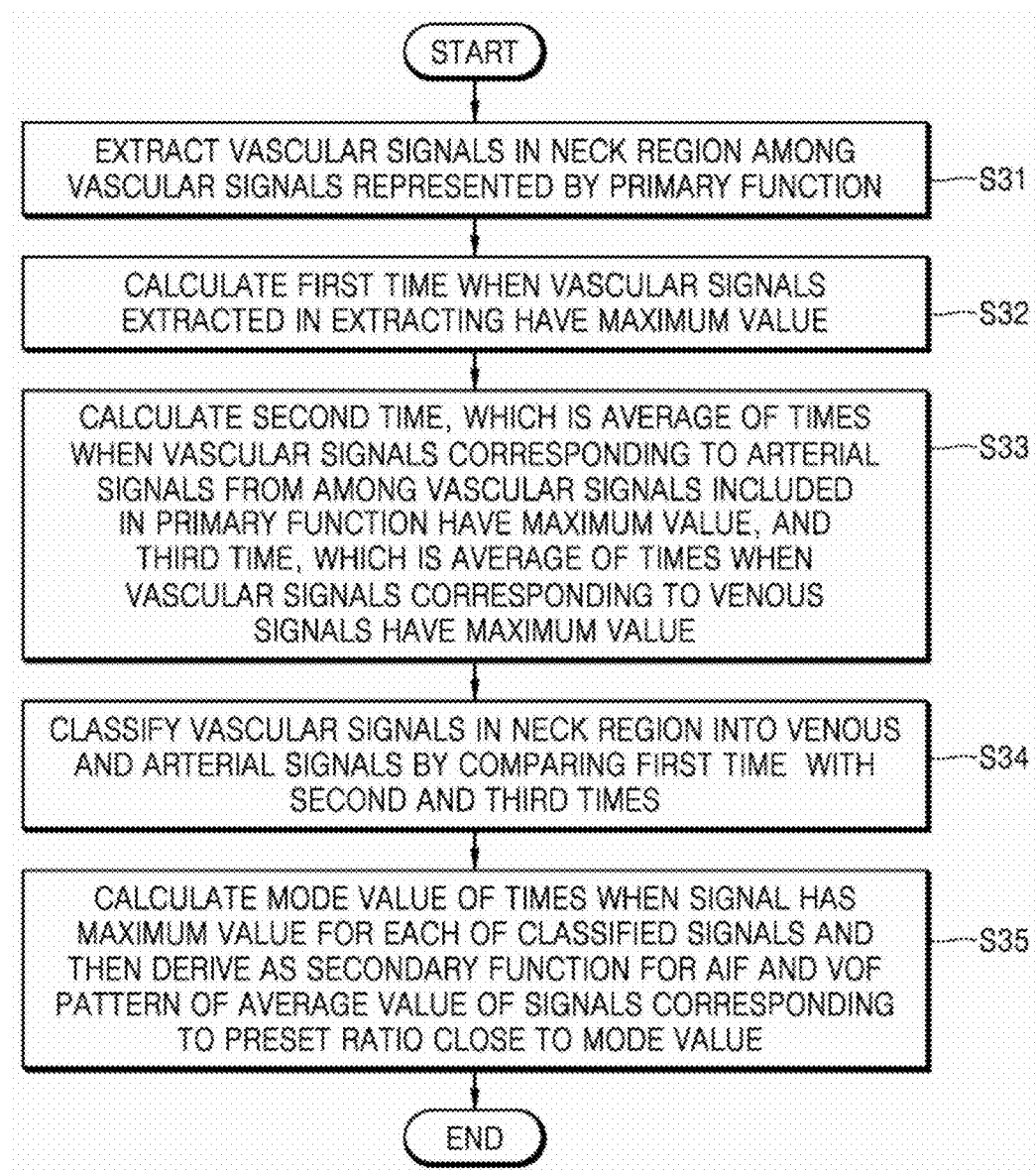
Figure 8:
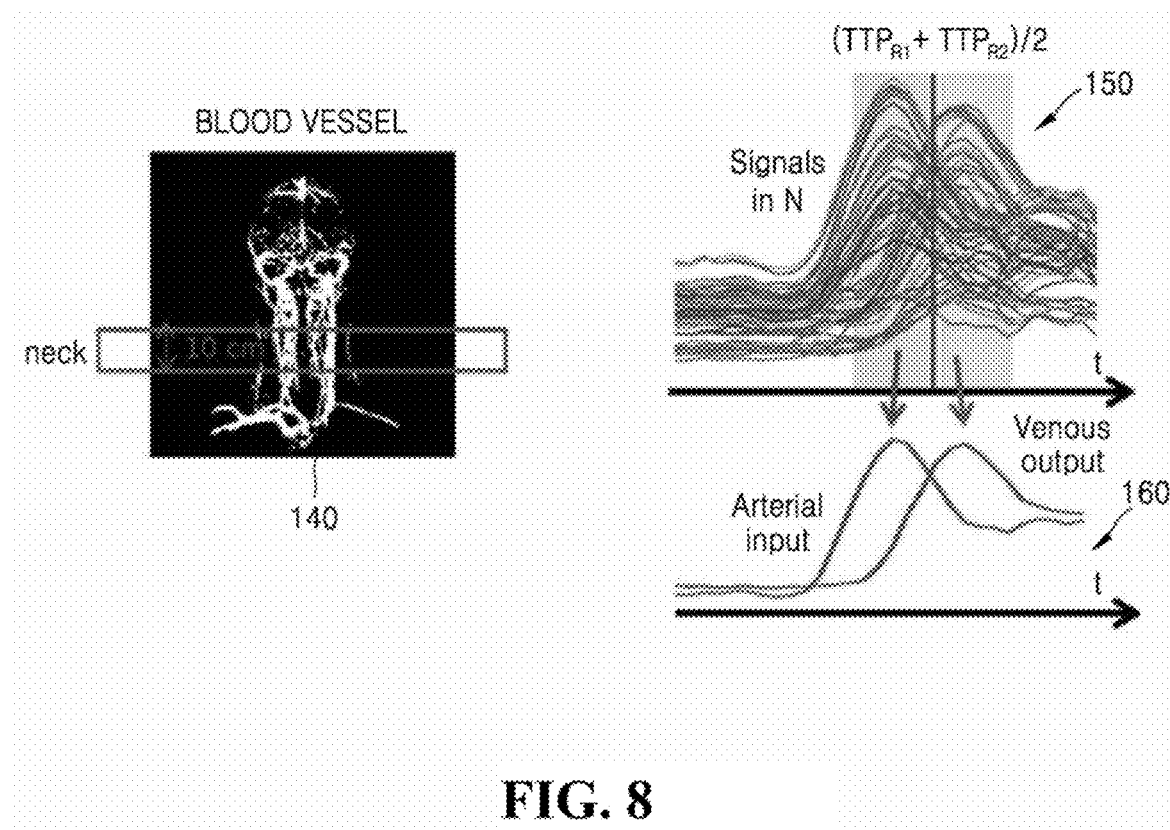

Referring to FIGS. 4 and 8, vascular signals 141 in a neck region determined according to the above-described technique are extracted from among vascular signals 140 represented by a primary function are extracted (S31).

Subsequently, a first time when the vascular signals extracted in step S31 have a maximum value is calculated (S32). Furthermore, a reference value is calculated for classifying the first time into arterial and venous signals.

In detail, a second time, which is an average of times when vascular signals corresponding to arterial signals from among vascular signals included in the primary function have a maximum value, and a third time, which is an average of times when vascular signals corresponding to venous signals from among the vascular signals included in the primary function have a maximum value, are calculated (S33).

After calculating the second and third times in step S33, the vascular signals in the neck region are classified into venous and arterial signals by comparing the first time 150 with the second and third times (S34).

In detail, referring to FIG. 8, a mean value $(TTP_{R1}+TTP_{R2})/2$ of the second time $TTPR_2$ and the third time $TTP_{R1}$ is calculated. A plurality of first times 150 are respectively computed for vascular signals. Among vascular signals 152 respectively corresponding to the calculated first times, vascular signals corresponding to the first times 150 that are less than $(TTP_{R1}+TTP_{R2})/2$ are classified as arterial signals while vascular signals corresponding to the first times 150 that are greater than $(TTP_{R1}+TTP_{R2})/2$ are classified as venous signals.

After performing step S34, a mode value of times when a signal has a maximum value is calculated for each of the classified signals, and then a pattern of an average value of signals corresponding to a preset ratio (e.g., 50%) close to the calculated mode value is obtained as a secondary function 160 for an AIF and a VOF (S35).

According to the above-described method, an AIF and a VOF are initially derived in a region near the heart and a head region where arterial and venous signals are dominantly distributed, and then an AIF and a VOF in a neck region are finally obtained by reflecting the derived AIF and VOF in vascular signals from the neck region to be observed.

According to the embodiments of the present disclosure, arterial and venous blood flow in a region where blood flow is to be analyzed may be accurately derived as a mathematical function. The mathematical function may be used to extract various pieces of information related to hemodynamics and be used in a visualization process such as demonstrating an image and a difference image at a meaningful specific time point. Thus, the mathematical function may be used in various diagnoses and treatments during analysis of blood flow.

A function for the above-described method of analyzing blood flow by using a medical image according to the embodiments of the present disclosure may be executed by a built-in application installed in a user terminal (which may include programs included in a built-in platform or an operating system) or may be executed by an application (i.e., a program) that is directly installed in the user terminal by the user via an application providing server such as an application store server or a web server related to a corresponding application or service. In this regard, the function for the method of analyzing blood flow by using a medical image according to the a embodiments may be implemented as applications (i.e., programs) that are basically installed or directly installed by a user in a user terminal and may be recorded in a computer-readable recording medium for the user terminal or the like.

Although it has been described above that all components of an embodiment of the present disclosure are combined as or combined to operate as a single one, the present disclosure is not limited to the embodiment. In other words, within the scope of the present disclosure, at least one of all the components thereof may be selectively combined to operate. Furthermore, all of the components may each be also implemented as an independent hardware, while some or all of the components may be selectively combined to be implemented as a computer program having a program module for performing some or all of the functions combined in one or a plurality of hardware. Codes or code segments that constitute the computer program may be easily deduced by those of ordinary skill in the art. The computer program may be stored in computer readable media and be read and executed by a computer to thereby realize an embodiment of the present disclosure. Examples of the computer readable media include magnetic recording media, optical recording media, etc.

It will be further understood that the terms "comprise," "consist of," or "have," when used in this specification, imply the presence of stated elements. Thus, when a part "comprises," "consists of," or "has" an element, unless there is a particular description contrary thereto, the part can further include other elements, not excluding the other elements. Unless otherwise defined, all terms (including technical and scientific terms) used herein have the same meaning as commonly understood by those of ordinary skill in the art to which the present disclosure belongs. It will be further understood that commonly-used terms, such as those defined in dictionaries, should be interpreted as having a meaning that is consistent with their meaning in the context of the relevant art and will not be interpreted in an idealized or overly formal sense unless expressly so defined herein.

While the present disclosure has been particularly shown and described with reference to exemplary embodiments thereof, it will be understood by one of ordinary skill in the art that various modifications and changes in form and details may be made therein without departing from the spirit and scope of the present disclosure. Thus, it should be understood that the exemplary embodiments described in the present disclosure should be considered in a descriptive sense only and not for purposes of limitation, and the scope of the present disclosure is not limited by the exemplary embodiments. The scope of the present disclosure should be defined by the following claims, and all technical ideas within the scope of the following claims and their equivalents will be construed as being included in the scope of the present disclosure.

The invention claimed is:

1. A method of analyzing blood flow by using a medical image, the method comprising:
    determining a position of a blood vessel from four-dimensional medical image data that is obtained by combining data of three-dimensional medical images of a patient's body captured at a preset period;
    deriving a primary function for an arterial input function and a venous output function by using a vascular signal in a head region and a vascular signal in a heart region from among vascular signals included in the three-dimensional medical image data for the position of the blood vessel determined in the determining; and
    deriving a secondary function that is a final function for the arterial input function and the venous output function by using the primary function and a vascular signal in a neck region,
    wherein the deriving of the secondary function comprises:
    extracting vascular signals in the neck region from among vascular signals represented by the primary function;
    calculating a first time when the vascular signals extracted in the extracting have a maximum value;
    calculating a second time, which is an average of times when vascular signals corresponding to arterial signals from among the vascular signals included in the primary function have a maximum value, and a third time, which is an average of times when vascular signals corresponding to venous signals from among the vascular signals included in the primary function have a maximum value;
    classifying the vascular signals in the neck region into venous and arterial signals by comparing the first time with the second and third times; and
    calculating a mode value of times for each of the classified vascular signals when the classified vascular signal has a maximum value, and then deriving a pattern of an average value of signals corresponding to a preset ratio close to the calculated mode value as the secondary function for the arterial input function and the venous output function.

2. The method of claim 1, wherein the determining of the position of the blood vessel comprises determining, as pixels constituting the blood vessel from among pixels constituting the four-dimensional medical image data, pixels ranked high with respect to a preset ratio in an order of a difference value between a maximum value and a minimum value of a signal magnitude according to time.

3. The method of claim 1, further comprising:
    generating an average image across all time frames based on the four-dimensional medical image data captured for each time frame;
    selecting pixels having signals with a magnitude greater than a preset threshold from the generated average image and then generating a mask image by applying a median filter to a region composed of the selected pixels; and
    determining, as the neck region, a region of a preset second height including a region having a smallest number of pixels from among regions excluding a top image and a bottom image of a preset first height from the generated mask image.

4. The method of claim 1, wherein the deriving of the primary function comprises:
    deriving, as the primary function for the venous output function, a function representing a pattern of an average value of vascular signals in a position of an upper blood vessel having a first height preset with respect to an image in the four-dimensional medical image data; and
    deriving, as the primary function for the arterial input function, a function representing a pattern of an average value of vascular signals in a position of a lower blood vessel having the first height preset with respect to the image in the four-dimensional medical image data.

* * * * *